United States Patent
Preikschat

[19]

[11] Patent Number: 5,829,754
[45] Date of Patent: Nov. 3, 1998

[54] SEALING AND FLOW INDUCING HUB ASSEMBLY

[76] Inventor: Ekhard Preikschat, 1940 - 124th Ave. N.E.,#A-102, Bellevue, Wash. 98005

[21] Appl. No.: 805,268

[22] Filed: Feb. 22, 1997

[51] Int. Cl.⁶ ............................. F16J 15/54; G01N 11/14
[52] U.S. Cl. ....................... 277/408; 73/54.32; 73/54.35
[58] Field of Search ............................... 416/223 R, 235; 68/134; 277/408, 391, 303; 73/54.23, 54.26, 54.28, 54.32, 54.03, 54.31, 54.33, 54.34, 54.35

[56] References Cited

U.S. PATENT DOCUMENTS

| | | | |
|---|---|---|---|
| 3,455,145 | 7/1969 | Gustafsson | 73/54.35 |
| 4,183,541 | 1/1980 | Wentworth | 277/391 X |
| 5,600,058 | 2/1997 | Preikschat et al. | 73/54.32 |
| 5,684,247 | 11/1997 | Preikschat | 73/54.32 |

*Primary Examiner*—Randolph A. Reese
*Assistant Examiner*—Gary Grafel
*Attorney, Agent, or Firm*—Dean A. Craine

[57] ABSTRACT

A hub assembly with improved sealing and anti-clogging properties comprising a housing body with a central, longitudinal aligned bore. In the embodiment described herein, a rotating shaft unit on a consistency transmitter is disposed inside the central bore. A flow cavity is formed on the distal end of the housing body which directly communicates with the central passageway of a pipeline containing flowing fluid material. The flow cavity is sufficient in size so that fluid material inside the pipeline may freely flow therein during use. Located around the distal opening of the housing body is an inner bushing made of graphite material. Located immediately adjacent to the inner bushing is a compressible bellows seal which imparts a force against the adjacent, outer surface of the inner bushing. The bellows seal which rotates with the rotating drive unit, has a smooth silicone-carbide end surface which is pressed tightly against the end surface on the stationary inner bushing thereby forming a tight seal. A protective shroud is disposed over the bellows seal to adjustably hold the bellows seal on the outer drive shaft and to prevent fluid material from leaking between the drive shaft, the bellows seal, and the inner bushing. Formed on the outer surface of the shroud is a spiral groove which induces an outward flow of fluid material located within the flow cavity on the housing body towards the back side of a low drag coefficient impeller attached to the distal end of the outer drive shaft.

14 Claims, 3 Drawing Sheets

SEALING AND FLOW INDUCING HUB ASSEMBLY

BACKGROUND OF THE INVENTION

1. Field of the Invention

The present invention relates to hub assemblies used in fluid handling devices, and more particularly, with hub assemblies used with devices that measure the viscosity or consistency of multi-phase material flowing in a pipeline.

2. Description of the Related Art

In the pulp and paper industry, the preparation and control of a pulp stream depends directly on the consistency of the moving pulp slurry. For example, the addition of bleaching additives, of retention aids, of various filler, starches and additives is all based on the consistency of a pulp slurry. To date, the most accurate measurement of consistency is still based on a mechanical measurement of the shear forces exerted by the moving pulp stream on a sensing element.

Large boats and freighters are typically powered by large, oil-fired industrial boilers which use low grade, bunker fuel oils as the primary fuel. Bunker fuel oils are the residual grades of the petroleum distillation process and can have a very high viscosity. These types of fuel oils can only be injected into a boiler if they are pre-heated to sufficiently reduce their viscosity. The efficiency of the burning process directly depends on how well the bunker fuel oil can be made into a mist and how uniformly it can be injected into the boiler—both of these factors depend on the viscosity of the bunker fuel oil.

It has been found that both pulp consistency and fuel-oil viscosity can be determined by measuring the torque on the shaft of a rotating impeller. When consistency (or viscosity) increase, the shear forces on the rotating impeller increases and it takes a higher driving force (torque) to rotate the impeller. Commercial devices are available to affect such a measurement, such as a consistency transmitter type MEK-41 manufactured by BTG, a Swedish company, and a rotating viscosity meter manufactured by Brookfield, a USA company. The former device uses a sensing shaft concentrically mounted within a drive shaft. A shear force measuring element (impeller) is mounted on the exposed end of a "sensor shaft" which is positioned directly into the moving pulp stream or fuel-oil. The sensor shaft rotates with the same rotational velocity as the outer shaft and is loosely coupled thereto. The outer shaft provides the main rotational driving force to the impeller and shields the sensor shaft from the frictional forces between the drive shaft and the outer gasket material, which prevents the pulp slurry from entering the housing of the sensor unit.

In a typical implementation, the relative rotational motion between the inner sensor shaft and the outer drive shaft is sensed and a counter-torque is applied to the sensor shaft so that it will rotate at exactly the same rotational velocity as the drive shaft. This counter-torque is equal and opposite to the torque on the sensor shaft produced by the shear forces of the pulp slurry on the rotating impeller. In the prior art, this counter-torque is not based on an absolute measurement of torque, but rather on secondarily deduced factors as measured by an electronic transducer or a rotating pneumatic transducer operating on the flapper-nozzle principle.

While this technology has long been used and accepted by the industry as the best and most accurate method of measuring consistency, it has two fatal draw-backs—lack of durability and reliability. Pulp slurry is very abrasive and corrosive which limits the lifetimes of the seals and gaskets used to isolate the rotating shafts used in the machinery. If the pulp slurry enters the sensor housing, the sensitive electronic equipment contained therein will be damaged which forces the entire production line to be shut down. For a large paper machine, the costs of such a shutdown is measured in the thousands of dollars per work shift. Therefore, it is important to provide a means to reduce or limit abrasion and corrosion.

Recently, an improved rotating consistency transmitter and method have been developed by APPA SYSTEMS, Inc. of Bellevue, Wash., (see U.S. Pat. No. 5,600,058) which determines the viscosity or consistency of a multi-phase material flowing in a pipeline by measuring the amount of torque generated on a rotating shaft disposed in the multi-phase material. Unfortunately, tests with this transmitter have shown that multi-phase material often penetrates the bushings, seals and gaskets used in the device. In addition, tests have also shown that, with continued use, the multi-phase material can collect in the region of the rotating shaft between the transmitter's impeller and the outer seal on the hub assembly which produces undesirable friction on the rotating shaft and outer seal. This friction reduces the life span of the outer seal. Therefore, a hub assembly with improved sealing and anti-clogging features is needed.

It should be understood that even though this invention makes specific reference to it being used on a state of the art consistency transmitter described in U.S. Pat. No. 5,600,058, it can also be used on other devices or machinery handling fluid materials.

SUMMARY OF THE INVENTION

It is, therefore, a general object of the present invention to provide a hub assembly for a fluid material handling device.

It is another object of the present invention to provide a hub assembly with improved sealing features and anti-clogging features.

These and other objects of the invention are met by providing a hub assembly designed to be used with a consistency transmitter as described in U.S. Pat. No. 5,600,058. This consistency transmitter, shown in FIG. 1 and generally denoted as 4, is attached to a port on a main pipeline, denoted as 2, through which fluid material flows. The consistency transmitter 4 includes a composite, rotating shaft unit 6 made up of three, concentrically aligned shafts—an outer drive shaft 22, a middle sensor shaft 23, and an inner reference shaft 24, shown more clearly in FIG. 2. The three shafts 22–24 are connected together so that when the outer drive shaft 22 is rotated, the middle sensor shaft 23 is rotated and causes, in turn, the inner reference shaft 24 to rotate. An impeller (I) is attached to the distal end of the middle sensor shaft 23. When fluid material flows in the main pipeline 2 and is in contact with the impeller (I), rotation of the impeller (I) is impeded, thereby producing a torque across the middle sensor shaft 23. This torque causes a twisting action on the middle sensor shaft 23 which can be determined by measuring the angular displacement between the outer drive shaft 22 and the inner reference shaft 24. An electric motor 5 is connected to the outer drive shaft 22 while a cover box 7 houses the optical discs used to measure the angular displacement of the outer drive shaft 22 and the inner reference shaft 24.

As shown more clearly in FIG. 3, the three shafts form the elongated rotating shaft unit 6 which extends through the opposite ends of a cylindrical shape rotating shaft housing 8. During assembly, the rotating shaft unit 6 and housing unit 8 are longitudinally aligned inside an installation assembly 10. The installation assembly 10 is used to easily connect and disconnect the consistency transmitter 4 to the main pipeline 2. The installation assembly 10 is connected to a mounting flange located on the outside surface of gate valve 12. The gate valve 12 is connected to a mounting saddle 13 on the main pipeline 2.

During assembly of the rotating shaft unit 6, an end cap 14 is attached to the distal end of the outer drive shaft 22, as shown in FIG. 2. A central hole 30 is formed in the end cap 14 through which the neck portion 33 of the plug 31 extends. The ends of the middle sensor shaft 23 and inner reference shaft 24 are attached to the body of a plug placed into the distal end of the rotating shaft unit 6. A double O-ring bushing 36 is disposed inside the distal end of the outer drive shaft 6 which holds the plug 31, the middle sensor shaft 23, and the inner reference shaft 24 co-axially aligned inside the outer drive shaft 22. The double O-ring bushing 36 also acts to prevent leakage of fluid material inside the rotating shaft unit 6.

The herein described hub assembly is an adjunct to the consistency transmitter described above to prevent leakage and clogging. The hub assembly is disposed between the consistency transmitter's rotating shaft housing unit and the central passageway inside the main pipeline. The hub assembly includes a cylindrical housing body with a central, longitudinal aligned bore formed therein. The cylindrical housing body encloses the portion of the rotating shaft unit that extends distally from the rotating shaft housing unit. The proximal end of the rotating shaft unit is connected to a motor while the distal end of the rotating shaft unit extends a short distance into the pipeline's central passageway. Formed on the distal end of the hub assembly's housing body is a concave-shaped, flow cavity which is sufficient in size and shape so that fluid material located inside the pipeline may freely flow therein during use.

Attached over the proximal and distal openings into the central bore in the housing body is an inner seal and a low friction, inner bushing, respectively. In one embodiment, the inner bushing is made of hard, smooth graphite material. Located distally and adjacent to the inner bushing is a bellows seal. Attached or formed over the proximal end of the bellows seal is a smooth, silicone-carbide layer. During assembly, the bellows seal and inner bushing are positioned adjacently around the rotating shaft so that the silicon carbide layer is in contact with the distal end of the inner bushing to form a durable, low friction interface. The amount of sealing pressure exerted by the bellows seal against the inner bushing may be adjusted by adjusting the compressive force exerted by the bellows seal against inner bushing.

A protective shroud is disposed longitudinally over the bellows seal. The shroud acts as a protective shield by preventing abrasive fluid material from leaking between the drive shaft, the bellows seal, and the outer bushing. A locking means is provided between the shroud and the bellows seal to fix the bellows seal in position to the rotating shaft unit.

During use, the inner bushing is stationary over the distal end of the housing body while the bellows seal rotates with the rotating shaft unit. As the bellows seal rotates, heat builds up on the two contacting surfaces between the bellows seal and the inner bushing. To dissipate this heat, an optional cooling means is provided. In the preferred embodiment, the optional cooling means includes a port connected to the housing body which allows a coolant to slowly circulate inside the central bore. The inner bushing includes an O-ring member enabling the inner bushing to act as an outer seal to hold the coolant inside the central bore.

Formed on the outer surface of the shroud is a flow inducing means designed to induce the outward flow of fluid material located within the flow cavity on the hub body. As the outer drive shaft is rotated, fluid material located within the flow cavity flows towards the back side of the impeller thereby preventing clogging around outer drive shaft.

In order to take full advantage of the flow inducing feature on the hub assembly, the impeller is modified to include two semi-circular blades perpendicularly aligned and attached along the peripheral edge of a round, rigid disk. The rigid disk is perpendicularly aligned and attached to the distal end of a plug member which extends through a end cap on the distal end of the outer drive shaft and connects to the middle sensor shaft and inner reference shaft. The blades which are attached to opposite sides of the rigid disk, have semi-circular outer surfaces which makes them as stream-lined as possible and to prevent debris from collected on their leading and trailing edges. The outer peripheral edge of the rigid disk is beveled along two surfaces to reduce the drag co-efficiency.

DESCRIPTION OF THE PREFERRED EMBODIMENT(S)

Figure 1:
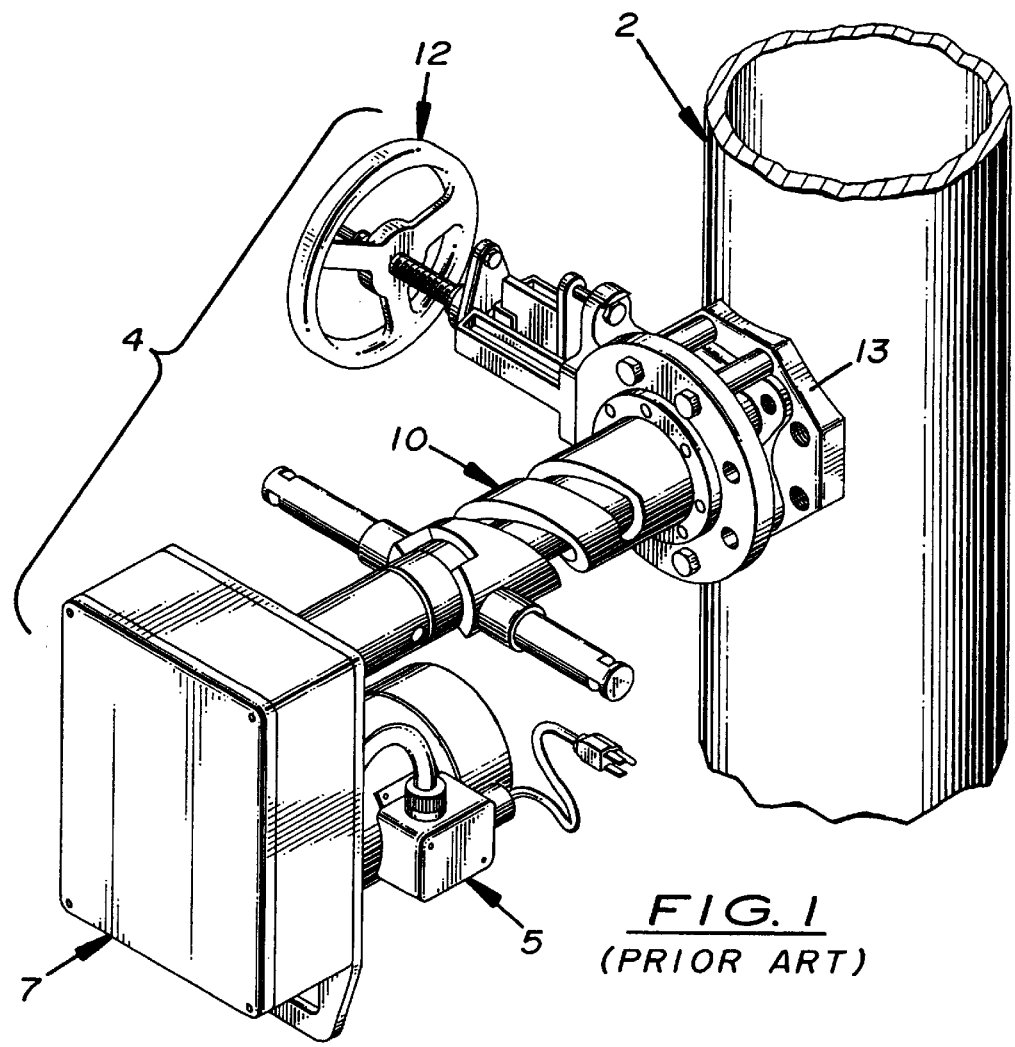
FIG. 1 is a perspective view of the consistency transmitter found in the prior art attached to a section of main pipeline.
Figure 2:
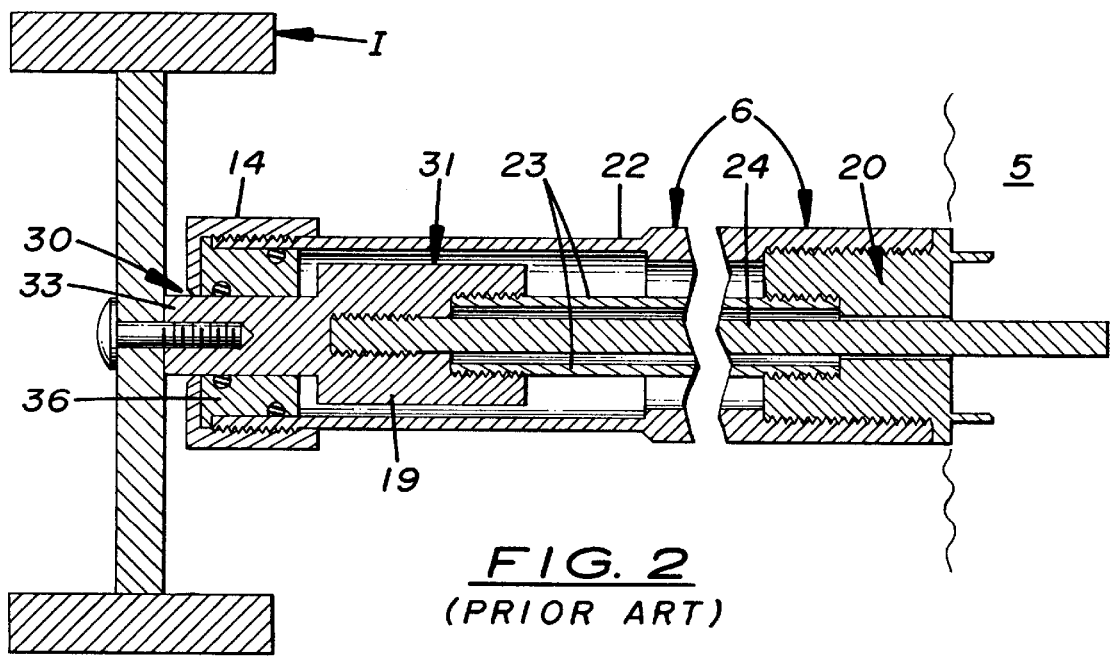
FIG. 2 is a partial, sectional, side elevation view of the distal portion of the rotating shaft unit found in the prior art.

The present invention in one embodiment finds preferred usage as a hub assembly for a rotating consistency transmitter 4 shown in FIGS. 1 and 2, and as described in U.S. Pat. No. 5,600,058, which now, is incorporated by reference herein.

Figure 3:
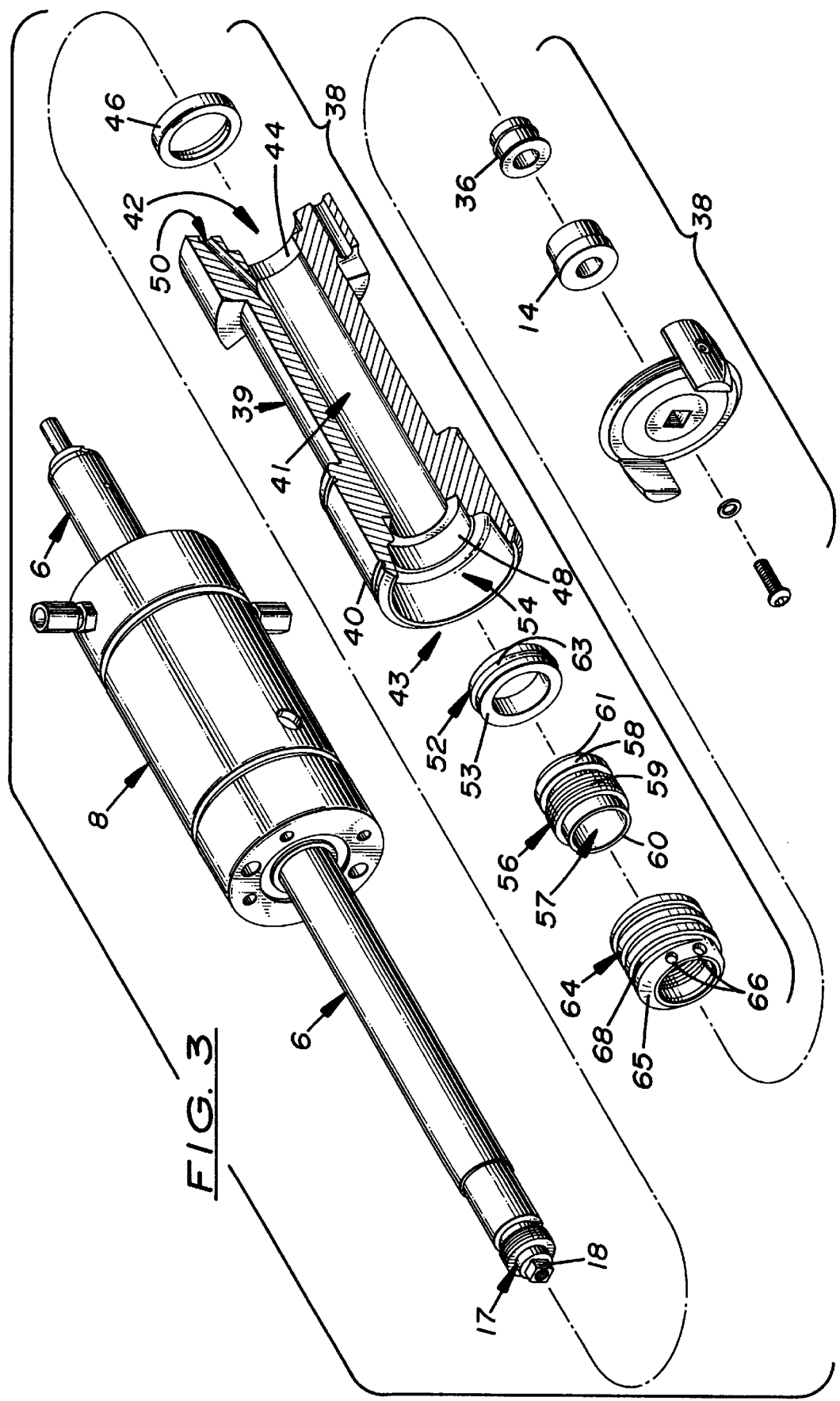
FIG. 3 is an exploded side elevation view, partly in section, showing the improved hub assembly described herein.
Figure 4:
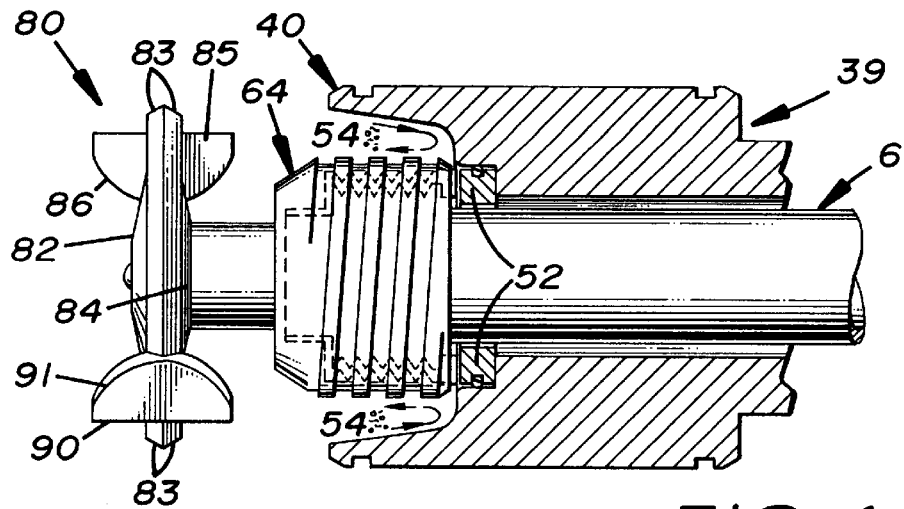
FIG. 4 is partial, sectional, side elevation view of the distal portion of the hub assembly showing the relative position of the shroud over the compressing means.

FIG. 3 shows an exploded view of the hub assembly 38 which includes a cylindrical-shaped housing body 39 made of aluminum or similar material. The length of the housing body is sufficient so that the distal end of the rotating shaft unit 6 is disposed inside the pipeline. Formed inside the housing body 39 is a longitudinally aligned central bore 41 with opposite proximal and distal openings 42, 43, respectively. The diameter of the central bore 41 is sufficient to closely enclose the rotating shaft unit 6 when inserted there through. Formed around the proximal opening 42, is an inner seal seat 44 designed to accept an inner seal 46. The inner seal 46 is inserted into the inner seal seat 44 and acts as a seal to prevent the coolant circulating inside the central bore 41 from leaking therefrom.

Facing outward and around the distal opening 43 is an O-ring seat 48 designed to accept an inner bushing 52. During assembly, the inner bushing 52 is inserted into the O-ring seat 48. The inner bushing is made of durable, low friction material, such as graphite.

The distal end 40 of the housing body 39 is recessed thereby forming a concave-shaped, flow cavity 54 which directly communicates with the central passageway located inside the main pipeline. The flow cavity 54 is sufficient in size so that fluid material inside the main pipeline may freely flow therein during use.

Located around the rotating shaft unit 6 and positioned distally and adjacent to the inner bushing 52 is an adjustable sealing means, herein after known as a bellows seal 56. The bellows seal 56 is cylindrical-shaped and includes a central passageway 57 to allow the bellows seal 56 to move longitudinally on the rotating shaft unit 6. The bellows seal 56 includes three integrally formed parts—an inward extending portion 58 with a silicon carbide surface 61, a collapsible bellows section 59, and an outward extending neck portion 60. In the preferred embodiment, the bellows seal 56 is a Rotating Alloy—20 Bellows Seal, type 680, distributed by E,G & G Company, with a silicon carbide layer 61.

A protective shroud 64 is disposed over the bellows seal 56. The shroud 64 includes an outer retaining ring 65 with adjustable screws 66 which press the outer surface of the neck of the bellows seal 56 to lock the bellows seal 56 in a relative compressed position thereon. Formed on the outer surface of the shroud 64 is a flow inducing means designed to induce the outward flow of fluid material located within the flow cavity 54 on the housing body 39. In the preferred embodiment, the flow inducing means is a spiral groove 68 formed over the outer surface of the shroud 64. The direction of the spiral groove 68 is determined so that when the outer drive shaft 22 is rotated, fluid material located within the flow cavity 54 is entrained to flow towards the back side of the impeller thereby preventing clogging around outer drive shaft 22. The bellows seal 56 provides a compressive force which acts to keep the silicon carbide surface 61 in contact with the end graphite surface 53 on the inner bushing 52. The relative position of the bellows seal 56 on the rotating drive shaft 6 may be adjusted by moving the retaining ring 65 to adjust the compression force exerted by the bellows seal 56 against the inner bushing 52. In summary, the shroud 64 serves two purposes: (i) to cover and protect the bellows seal 56, and (ii) to act like an auger to induce the outward flow of fluid material from the flow cavity 54 and towards the back side of the impeller. By keeping this region clean, the abrasive action of the fluid material against the sealing surfaces is reduced.

During use, the inner bushing 52 is stationary over the distal end of the housing body 39 while the bellows seal 56 rotates with the rotating shaft unit 6. As the bellows seal 56 rotates, heat builds up on the two contacting surfaces, 53, 61 between the inner bushing 52 and the bellows seal 56, respectively. To dissipate this heat, an optional cooling means is provided. In the preferred embodiment, the optional cooling means includes a port 50 which communicates between the outside surface of the housing body 39 and the central bore 41 through which a coolant may be circulated into the housing body 39. When an optional cooling means is used, the inner bushing 52 is modified to include an outer O-ring member 63 which allows the inner bushing 52 to act as an outer seal to hold the coolant inside the central bore 41.

As discussed in U.S. Pat. No. 5,600,058, the shape of the rotating impeller determines how the impeller interacts with the fluid material. When the impeller rotates within the fluid material, there are several forces acting on the impeller: (1) the yield stress forces that result when a moving object causes a separation (or break-up) of the fibers within an interlocking fiber network (also referred to as "coherent flocculation"); (2) the frictional forces caused by the moving fiber stream pressing against the flat surface of the impeller; and, (3) the turbulence forces caused by the wake of the moving impeller.

Figure 5:
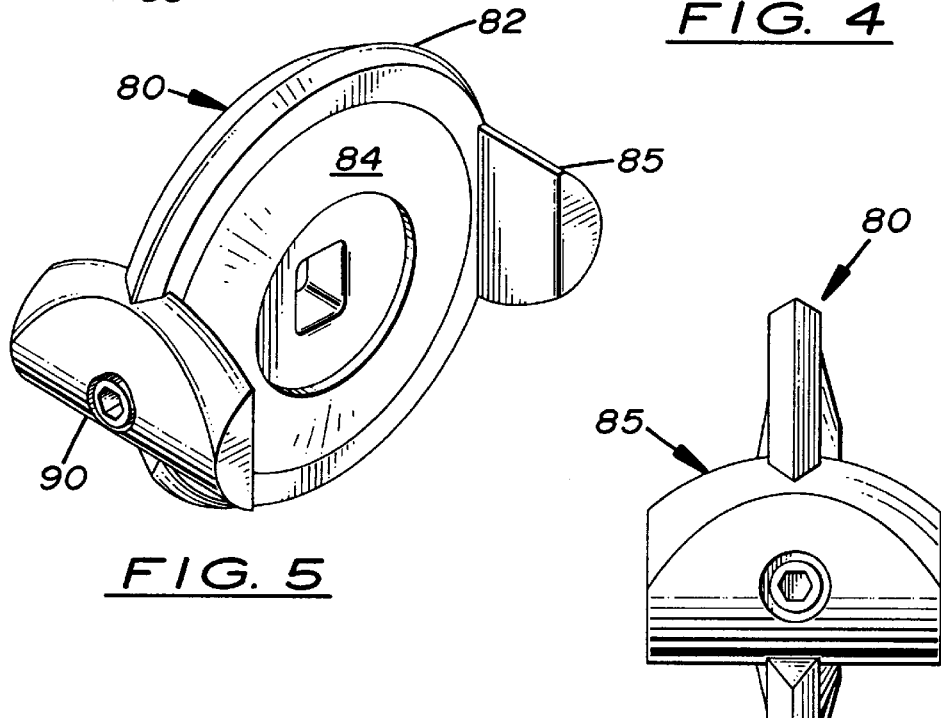
FIG. 5 is a perspective view of the impeller.
Figure 6:
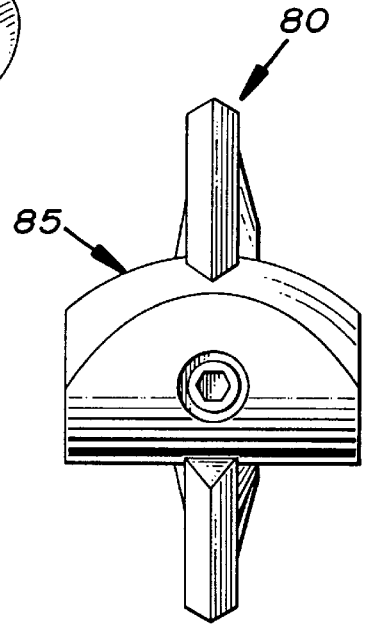
FIG. 6 is a side elevation view of the impeller shown in FIG. 5.

In summary, it is best to have an impeller that has a front edge of maximum length with the smallest surface area. A simple piano wire positioned so that its major axis is perpendicular to the flow would be an idealized implementation of such a geometry. However, a simple perpendicular structure, like a piano wire, would not work as it would cause pulp fibers to collect on the front surface. Instead, the front surface of the impeller must be self-cleaning. In FIGS. 5 and 6, novel impeller 80 is shown comprising two, semi-circular blades 85, 90 mounted to a circular, rigid disk 82 which is fastened to the neck portion 33 of the plug 31 shown in FIG. 2. It should be noted that not only is the overall shape of the blades 85, 90 semi-circular, but also the front edges are rounded to make them as stream-lined as possible and to prevent the collection of debris on the front edges 86, 91, respectively, of the blades 85, 90. Furthermore, the peripheral edge 83 of the rigid disk 82 is also beveled at two angles to reduce the drag coefficient. The back surface 84 of the rigid disk 82 may also be beveled and recessed to fit closely around the neck portion 33 of the plug 31 to prevent any debris from collecting between the rigid disk 80 and the neck portion 33. It was empirically determined that the drag coefficient of the impeller 80 is half as much when using the rigid disk 82 as compared to using a flat post to support the sensor blades.

Figure 7:
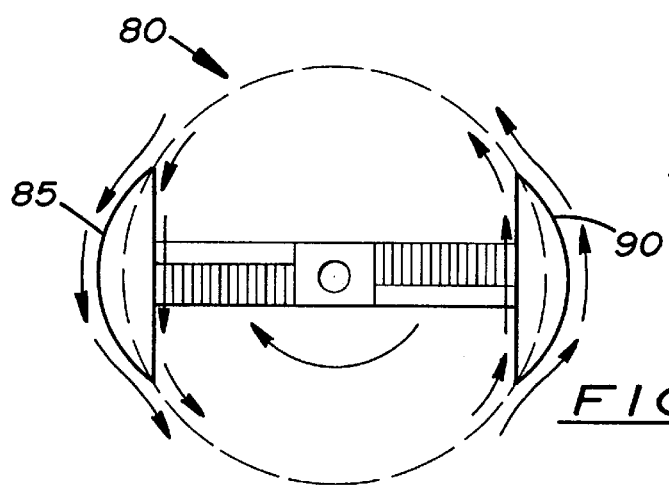
FIG. 7 is a front plan view of the impeller showing the flow pattern of fluid material over the blade.

By using at least two blades 85, 90, positioned opposite to each other, as shown in FIGS. 5 and 6, it is also important to note that the velocity effects caused by a moving fluid stream can be offset. With this arrangement, one blade 85 moves with the stream, while the other blade 90 moves against the stream thereby balancing each other as shown in FIG. 7. This balancing effect occurs when more than two blades are used so as long as the blades are positioned at equal angles around the circumference of the circle of rotation.

In compliance with the statute, the invention, described herein, has been described in language more or less specific as to structural features. It should be understood, however, the invention is not limited to the specific features shown, since the means and construction shown comprised only the preferred embodiments for putting the invention into effect. The invention is, therefore, claimed in any of its forms or modifications within the legitimate and valid scope of the amended claims, appropriately interpreted in accordance with the doctrine of equivalents.

I claim:

1. A fluid flow inducing hub assembly for a rotating drive shaft having one distal end disposed in a fluid material, said hub assembly comprising:

a. a housing body having a central bore, a distal end opening and a proximal end opening, said housing body having a flow cavity formed adjacent to said distal end opening;

b. a sealing means capable of sealing said rotating drive shaft against said housing body; and, c. a flow inducing means coupled to said rotating drive shaft capable of inducing the outward flow of fluid material located in said flow cavity when said rotating drive shaft is disposed in said fluid material and said rotating drive shaft is rotated said flow inducing means being a cylindrical-shaped shroud disposed over said sealing means and coupled to said drive shaft, said shroud having an outer surface with a spiral groove formed thereon capable of inducing the outward flow of fluid located in said flow cavity when said rotating drive shaft is rotated.

2. A hub assembly as recited in claim 1, wherein said sealing means is a bellows seal.

3. A hub assembly as recited in claim 2, further including said bellows seal including a silicon carbide sealing surface.

4. A hub assembly as recited in claim 3, further including said sealing means including an inner bushing disposed over said distal opening of said central bore.

5. A hub assembly as recited in claim 4, wherein said bushing is made of graphite material.

6. A hub assembly, as recited in claim 2, further including a locking means on said shroud capable of engaging said rotating drive shaft to hold said shroud and bellows seal in position on said rotating drive shaft.

7. A hub assembly, as recited in claim 2, further including said housing body having a cooling means capable of dissipating heat therein.

8. A hub assembly, as recited in claim 7, wherein said cooling means includes a port formed in said housing body enabling a coolant to flow therein, an inner seal attached over said proximal end of said central bore, and an O-ring member attached to said inner bushing to form a seal around said distal end of said central bore to prevent the leakage of the coolant from said housing body.

9. A hub assembly as recited in claim 1, further including an impeller having a rigid disk perpendicularly aligned and coupled to said distal end of said rotating drive shaft, said rigid disk having a two-beveled peripheral edge and at least two semi-circular blades aligned in a parallel manner and attached at opposite sides of said rigid disk.

10. A fluid flow inducing hub assembly for a rotating drive shaft having one distal end disposed in a fluid material, said hub assembly, comprising:

a. a housing body having a central bore, a distal end opening, and a proximal end opening, said housing body having a flow cavity formed adjacent to said distal end opening;

b. an inner bushing located around said distal end opening of said housing body;

c. a flow inducing means coupled to said rotating drive shaft capable of inducing the outward flow of fluid material located in said flow cavity when said rotating drive shaft is disposed in said fluid material and said rotating drive shaft is rotated; and, d. an impeller having a rigid disk perpendicularly aligned and coupled to the end of said rotating drive shaft, said rigid disk having a two-beveled peripheral edge and at least two semi-circular blades parallel aligned and attached at opposite sides of said rigid disk.

11. A hub assembly as recited in claim 10, further including an adjustable sealing means disposed between said inner bushing and said flow inducing means.

12. A hub assembly as recited in claim 11, wherein said flow inducing means is a cylindrical-shaped shroud disposed over and coupled to said drive shaft, said shroud having an outer surface with a spiral groove formed thereon capable of inducing the outward flow of fluid located in said flow cavity when said drive shaft is rotated.

13. A hub assembly, as recited in claim 12, further including said housing body includes a cooling means capable of dissipating heat therein.

14. A hub assembly, as recited in claim 13, wherein said cooling means includes a port formed in said housing body enabling a coolant to flow therein, a inner seal attached over said proximal end of said central bore, and an O-ring member attached to said inner bushing to form a seal around said distal end of said central bore to prevent the leakage of the coolant from said housing body.

* * * * *